United States Patent
Chao

(10) Patent No.: US 6,217,601 B1
(45) Date of Patent: Apr. 17, 2001

(54) ADJUSTABLE HEMOSTATIC STRAP

(76) Inventor: Richard C. C. Chao, No. 35-3, Lane 165, Sec. 1, Hsin-Sheng South Rd., Taipei (TW)

( * ) Notice: Subject to any disclaimer, the term of this patent is extended or adjusted under 35 U.S.C. 154(b) by 0 days.

(21) Appl. No.: 09/414,536

(22) Filed: Oct. 8, 1999

(51) Int. Cl.[7] .................................................. A61B 17/00
(52) U.S. Cl. ........................................................... 606/203
(58) Field of Search .................................... 606/203, 157, 606/151, 204; 24/170; 248/96; 224/163, 660, 667, 668, 669, 587, 250

(56) References Cited

U.S. PATENT DOCUMENTS

| | | | |
|---|---|---|---|
| 4,102,343 | * 7/1978 | Schneider | 606/203 |
| 4,125,115 | * 11/1978 | Mayo et al. | 606/203 |
| 5,314,437 | * 5/1994 | Hotsch | 606/157 |
| 5,535,485 | * 7/1996 | Kirchner | 606/203 |

* cited by examiner

Primary Examiner—Henry J. Recla
Assistant Examiner—(Jackie) Tan-Uyen T. Ho
(74) Attorney, Agent, or Firm—Bacon & Thomas,PLLC

(57) ABSTRACT

An adjustable hemostatic strap which includes a flat elastic band for fastening to the hand to compress the vessel when making a hypodermic injection, and a buckle for fastening the flat elastic band to the hand, the buckle including a plug member fixedly fastened to one end of the flat elastic band, and a socket member slidably mounted on the elastic band and secured to the flat elastic band at the desired location for receiving the plug member for enabling the elastic band to be firmly secured to the hand to compress the vessel.

4 Claims, 5 Drawing Sheets

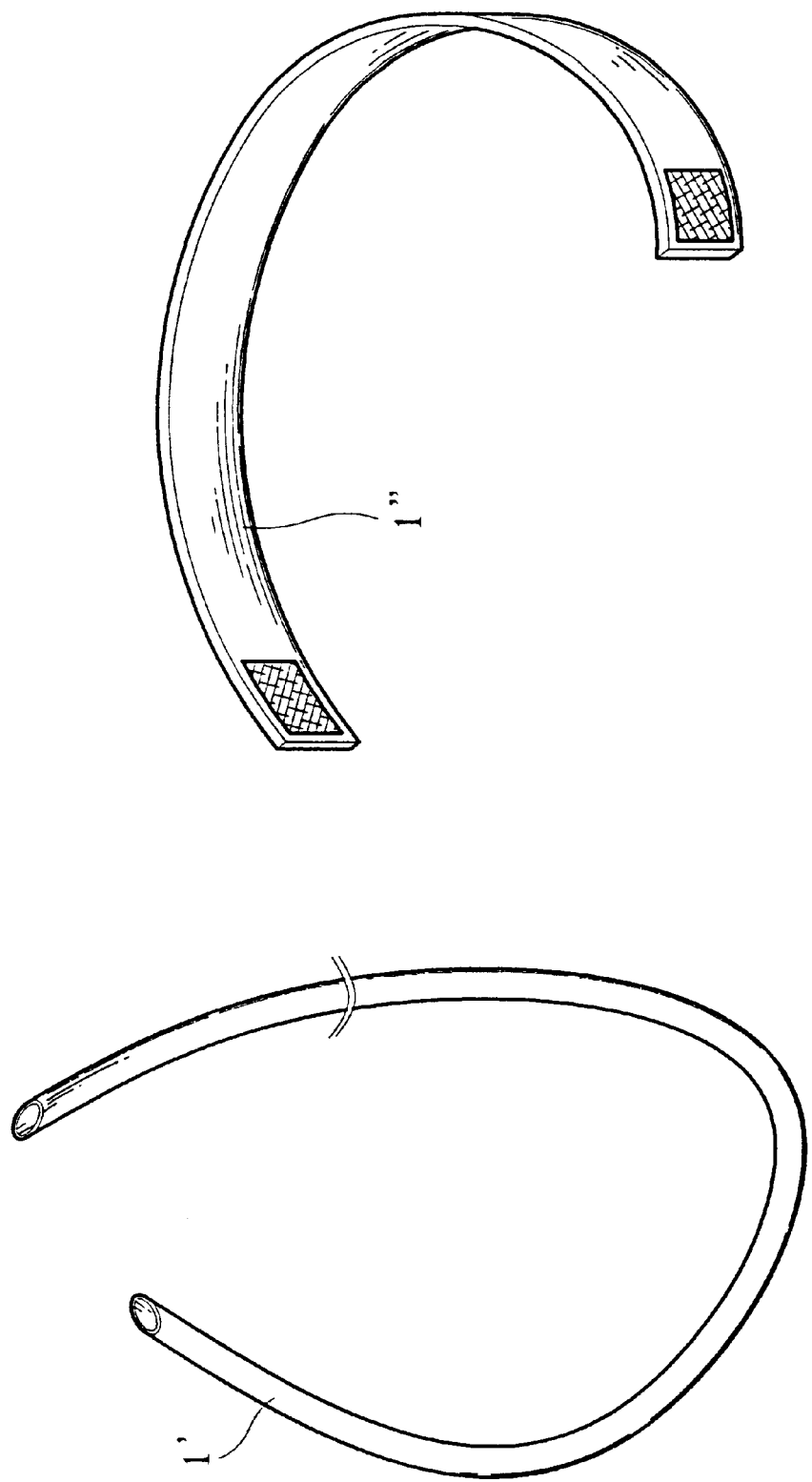

ADJUSTABLE HEMOSTATIC STRAP

BACKGROUND OF THE INVENTION

The present invention relates to a hemostatic strap, and more particularly to an adjustable hemostatic strap that can conveniently be adjusted to provide a suitable compressive force to the vessel.

Before taking a hypodermic injection or drawing blood from the vessel at the hand, a hemostatic tube 1' (see FIG. 1) or hemostatic strap 1" (see FIG. 2) may be used, and fastened to the hand to compress the vessel, so that the needle of the hypodermic syringe can be accurately pierced through the wall of the vessel into its inside. When blood flows backwards into the hypodermic syringe, the hemostatic tube 1' or strap 1" is unfastened, enabling the medicine to be injected into the vessel. However, the hemostatic tube 1' or strap 1" must be maintained fastened to the hand when drawing blood from the vessel. The hemostatic tube 1' shown in FIG. 1 is a rubber tube, which may stretch the skin when fastened to the hand, causing the skin injured. When unfastening the hemostatic tube 1', the hemostatic tube 1' may trip out suddenly, causing the skin to be injured again. Further, when fastening the hemostatic tube 1' to the hand, the hemostatic tube 1' tends to be twisted, causing the vessel to be deformed, and the needle of the hypodermic syringe may be forced to pierce through the vessel and to pass into the muscles. Because the hemostatic tube 1' is an elastic tube, it may fall out of the physician or nurse's pocket when the physician or nurse moves the body. The hemostatic strap 1" shown in FIG. 2 is a flexible strap having hook and loop materials at its two distal ends. Because the hemostatic strap 1" is a flat strap, it imparts a compressive force to the vessel evenly when installed. This structure of hemostatic strap 1" does not stretch the skin. However, it cannot be adjusted to impart a suitable compressive force to the vessel when installed.

SUMMARY OF THE INVENTION

The present invention provides an adjustable hemostatic strap, which can be conveniently adjusted to impart a suitable compressive pressure to the vessel without causing the skin to be stretched. According to one aspect of the present invention, the hemostatic strap comprises a flat elastic band, and a buckle for fastening the flat elastic band to the hand, enabling the tension of the elastic band to be conveniently adjusted to the desired level. According to another aspect of the present invention, a holding down member is fastened to the flat elastic band for holding down a medicated cotton pellet on the skin at the injected point. According to still another aspect of the present invention, an end piece is fixedly fastened to one end of the flat elastic band, the end piece having a hanging hole for hanging.

BRIEF DESCRIPTION OF THE DRAWINGS

FIG. 1 illustrates a hemostatic tube according to the prior art.

FIG. 2 illustrates a hemostatic strap according to the prior art.

DETAILED DESCRIPTION OF THE PREFERRED EMBODIMENT

Figure 3:
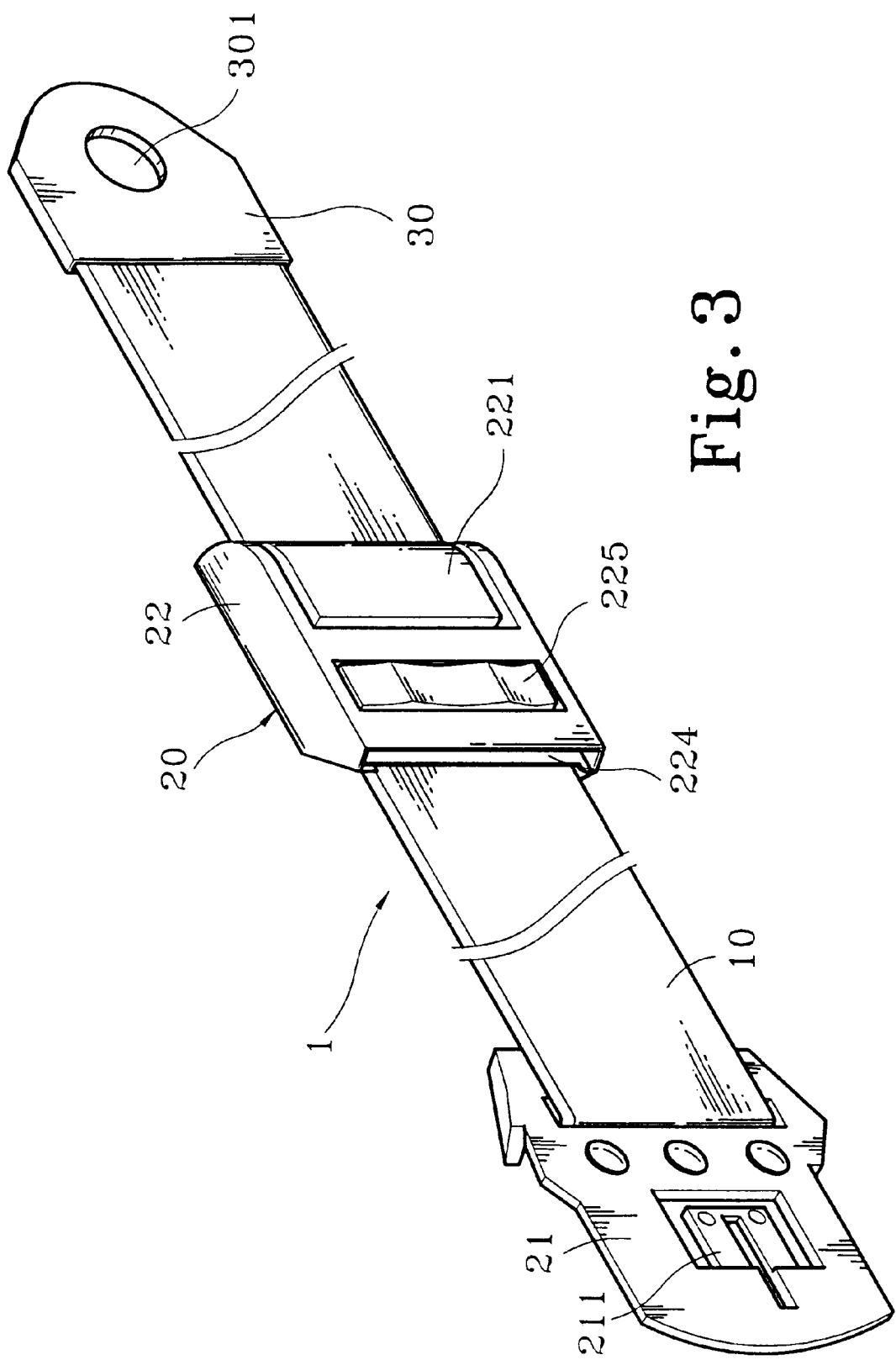
FIG. 3 is a perspective view of an adjustable hemostatic strap according to the present invention.
Figure 4:
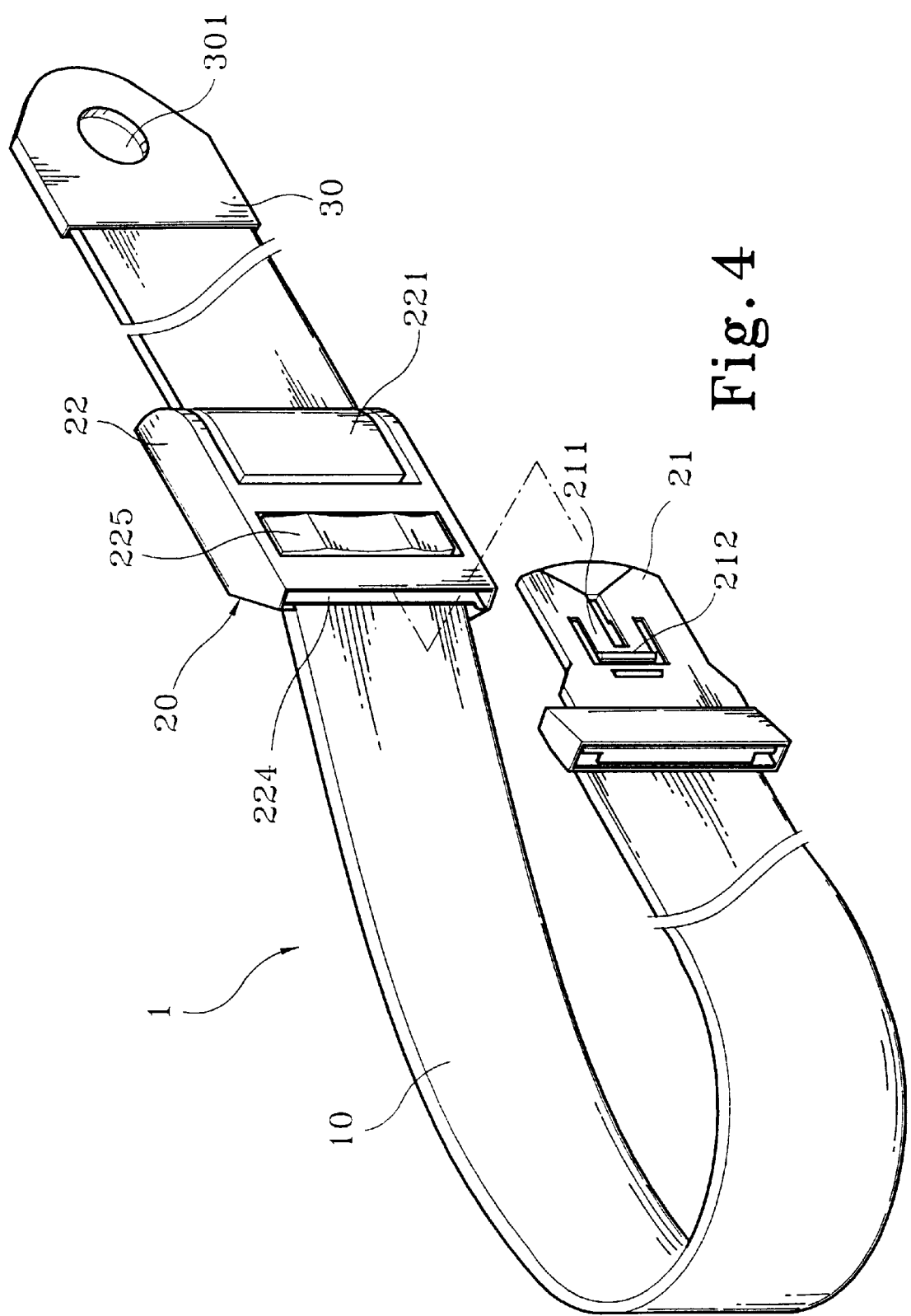
FIG. 4 is another perspective view of the adjustable hemostatic strap shown in FIG. 3.
Figure 5:
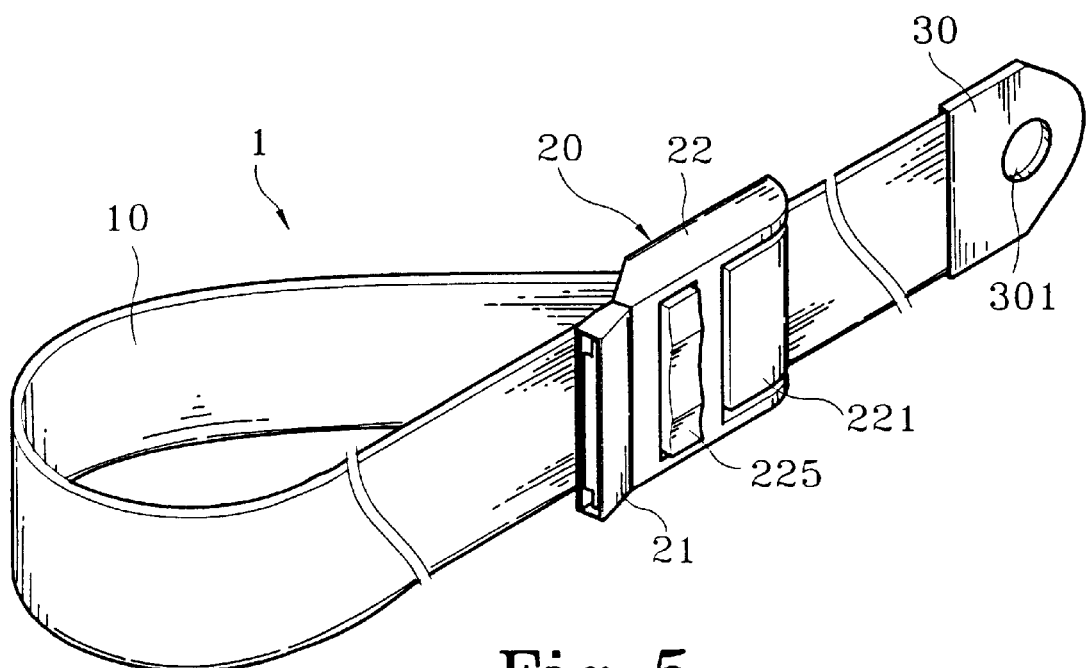
FIG. 5 shows the plug member fastened to the socket member at the flat elastic band according to the present invention.
Figure 6:
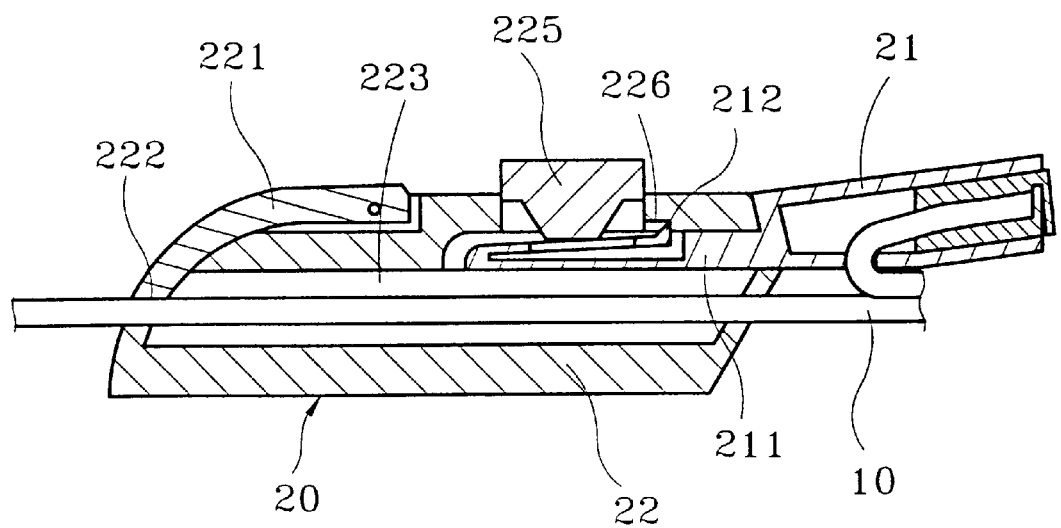
FIG. 6 is a sectional view of a part of FIG. 5.

Referring to Figures from 3 through 6, an adjustable hemostatic strap 1 is shown comprised of an elastic band 10, and a buckle 20. The elastic band 10 is a flat, elongated rubber band. A meshed fabric covering may be covered on the outside wall of the elastic band 10. The buckle 20 is comprised of a plug member 21 fixedly mounted on one end of the elastic band 10, and a socket member 22 slidably mounted on the elastic band 10 for receiving the plug member 21. When in use, the elastic band 10 is placed around the bleeding limb, and then the plug member 21 is plugged into the socket member 22 to secure the elastic band 10 to the bleeding limb, causing the elastic band 10 to compress the bleeding vessel.

The socket member 22 is sleeved onto the elastic band 10 and moved thereon to the desired location, comprising a clamping plate 221 having a serrated portion 222 meshed with the elastic band 10. Depressing the clamping plate 221 causes the serrated portion 222 to be turned with the clamping plate 221 and disengaged from the elastic band 10, enabling the socket member 22 to be moved on the elastic band 10. The socket member 22 comprises a receiving chamber 223 for receiving the plug member 21, a plug hole 224 through which the plug member 21 is inserted into the receiving chamber 223, a pressure element 225 suspended in the receiving chamber 223 at the top, and a retaining notch 226 inside the receiving chamber 223. The pressure element 225 is pushed upwards when inserting the plug member 21 into the receiving chamber 223 at the socket member 22. The plug member 21 comprises a backwardly upwardly projected protruding spring plate 211, and a retaining rib 212 at the free end of the protruding spring plate 211. When inserting the plug member 21 into the plughole 224, the protruding spring plate 211 is forced downwards for enabling the plug member 21 to be smoothly inserted into the receiving chamber 223. Upon insertion of the plug member 21 into the receiving chamber 223 in the socket member 22, the pressure element 225 is forced upwards, enabling the retaining rib 212 of the protruding spring plate 211 to be forced into engagement with the retaining notch 226 in the socket member 22. When connected, the segment of the elastic band 10 between the plug member 21 and the socket member 22 is arranged into the shape of a loop, and the other part of the elastic band 10 beyond the looped segment is the free end. When depressing the pressure element 225 with the hand, the retaining rib 212 is forced away from the retaining notch 226, enabling the plug member 21 to be disconnected from the socket member 22. Further, an end piece 30 is fixedly fastened to the free end, namely, the end opposite to the plug member 21. The end piece 30 has a hanging hole 301 for hanging on, for example, a hook (not shown).

The operation of the present invention is outlined hereinafter with reference to Figures from 3 through 6 again. The elastic band 10 is placed around the bleeding limb, then the plug member 21 is inserted through the plug hole 224 into the receiving chamber 223 in the socket member 22, enabling the elastic band 10 to be fastened to the bleeding limb, and then the clamping plate 321 is depressed with the thumb to disengage the serrated portion 222 of the clamping plate 321 from the surface of the elastic band 10, and at the same time the socket member 22 is pushed toward the bleeding limb with the forefinger and, the free end, namely, the end piece 30 is pushed in the reversed direction with the other three fingers, and therefore the elastic band 10 is adjusted to increase its compressive force against the bleeding limb (the bleeding vessel). If the bleeding limb feels uncomfortable, hold the grip the end piece 30 with the hand which is not injured, then stop the forefinger of the same hand at the socket member 22, and then press the clamping plate 221 with the thumb to disengage the serrated portion 222 from the elastic band 10, enabling the forefinger is pushed to move the socket 20 along the elastic band 10 toward the end piece 30, and therefore less pressure is give to the bleeding limb (bleeding vessel). When releasing the elastic band 10 from the bleeding limb, the pressure element 225 is depressed with the hand to disengage the retaining rib 212 from the retaining notch 226, enabling the plug member 21 to be disconnected from the socket member 22.

Because the elastic band 10 is a flat band, it will not be twisted when fastened to the bleeding limb, therefore a compressive force can evenly and positively be applied to the bleeding limb (bleeding vessel) to stop the limb from bleeding. When the hemostatic strap is used and fastened to the hand going to receive a hypodermic injection, the user can adjust the tension of the elastic band 10 by oneself. Further, because the compressive pressure is evenly given to the vessel when receiving a hypodermic injection, the vessel does not displace when the hemostatic strap is unfastened.

Figure 7:
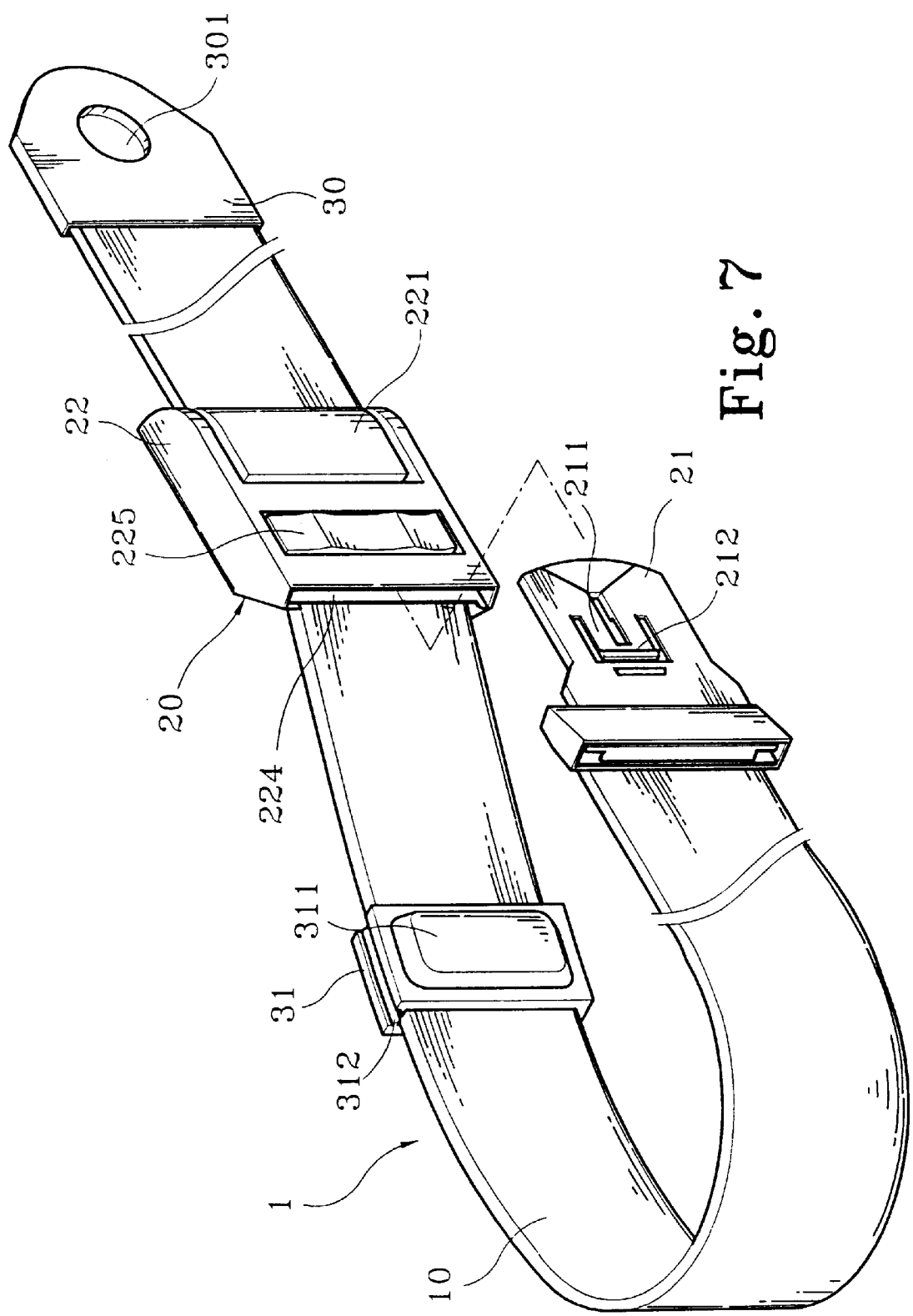
FIG. 7 shows a holding down member fastened to the flat elastic band of the adjustable hemostatic strap according to the present invention.

Referring to FIG. 7, a holding down member 31 is fastened to the elastic band 10 between the plug member 21 and the socket member 22. The holding down member 31 is shaped like an open-loop fitting the outside wall of the elastic band 10, comprising two springy retaining portions 312 at two ends thereof, and a pressure face 311 at one side. The springy retaining portions 312 define a gap through which the elastic band 10 can be inserted into the holding down member 31. The gap is narrower than the thickness of the elastic band 10, so that the holding down member 31 can be positively secured to the elastic band 10 after insertion of the elastic band 10 into the holding down member 31. After a hypodermic injection, a medicated cotton pellet can be inserted in between the pressure face 311 and the hand, and pressed on the pierced point at the hand by the pressure face 311 to stop bleeding.

What is claimed is:

1. An adjustable hemostatic strap comprising:

a flat elastic band for fastening to the hand of a user to compress a vessel, said flat elastic band having a first end and a second end;

a buckle for fastening said flat elastic band to the hand of the user for enabling said flat elastic band to compress the vessel, said buckle including a plug member fastened to the first end of said flat elastic band and a socket member mounted on and movable along said flat elastic band to dispose the socket member at a desired location on said flat elastic band for receiving said plug member; and a holding down member shaped like an open-loop and fastened to said flat elastic band, said holding down member including two springy retaining portions at two ends thereof for defining a gap through which said flat elastic band is inserted into said holding down member.

2. The adjustable hemostatic strap of claim 1 wherein said socket member comprises a clamping plate having a serrated portion meshed with said flat elastic band to secure said socket member firmly to said flat elastic band, said serrated portion being disengaged from said flat elastic band for enabling said socket member to be moved on said flat elastic band when said clamping plate is depressed.

3. The adjustable hemostatic strap of claim 1 wherein said socket member comprises a receiving chamber for receiving said plug member, a pressure element suspended in said receiving chamber at a top side, and a retaining notch disposed inside said receiving chamber for securing said plug member in position; said plug member comprises a backwardly upwardly projected protruding spring plate, and a retaining rib at said protruding spring plate for engagement with the retaining notch in said receiving chamber after insertion of said plug member into the receiving chamber in said socket member.

4. The adjustable hemostatic strap of claim 1 further comprises an end piece fixedly fastened to the second end of said flat elastic band, said end piece having a hanging hole for hanging.

\* \* \* \* \*